(12) United States Patent
Moulder et al.

(10) Patent No.: US 8,095,216 B1
(45) Date of Patent: Jan. 10, 2012

(54) SYSTEM TO CREATE ARBITRARY WAVEFORMS USING AN EXTERNAL INDUCTOR AND AN IMPLANTABLE MEDICAL DEVICE

(75) Inventors: J. Christopher Moulder, Encino, CA (US); Scott Salys, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 1138 days.

(21) Appl. No.: 11/858,365

(22) Filed: Sep. 20, 2007

(51) Int. Cl.
*A61N 1/362* (2006.01)

(52) U.S. Cl. ........................................ 607/33

(58) Field of Classification Search ............... 607/33
See application file for complete search history.

(56) References Cited

U.S. PATENT DOCUMENTS

| | | |
|---|---|---|
| 5,184,616 A | 2/1993 | Weiss |
| 5,470,341 A | 11/1995 | Kuehn et al. |
| 5,716,381 A | 2/1998 | Reggiardo |
| 5,725,560 A | 3/1998 | Brink |
| 5,733,310 A | 3/1998 | Lopin et al. |
| 6,175,765 B1 | 1/2001 | Sullivan et al. |
| 6,208,896 B1 | 3/2001 | Mulhauser |
| 6,563,377 B2 | 5/2003 | Butler |
| 2001/0031991 A1 | 10/2001 | Russial |
| 2003/0088281 A1 | 5/2003 | Ostroff et al. |
| 2003/0125773 A1 | 7/2003 | Havel et al. |
| 2003/0191504 A1* | 10/2003 | Meadows et al. .............. 607/33 |

OTHER PUBLICATIONS

First Office Action, mailed Jul. 5, 2006: Related U.S. Appl. No. 10/687,386.
Final Office Action, mailed Nov. 20, 2006: Related U.S. Appl. No. 10/687,386.
Advisory Action, mailed Feb. 12, 2007: Related U.S. Appl. No. 10/687,386.
Office Action, mailed Apr. 11, 2007: Related U.S. Appl. No. 10/687,386.

* cited by examiner

*Primary Examiner* — Carl H. Layno
*Assistant Examiner* — Jon-Eric C. Morales

(57) ABSTRACT

An implantable stimulation system includes a stimulation current generator encased in an implantable housing, one or more stimulation leads to deliver therapeutic stimulation from the generator to target patient tissue, and inductive elements arranged to condition the stimulation for delivery to the target tissue with increased efficiency and reduced pain sensation. The inductive elements are arranged external to the housing and integral with one or more of a stimulation lead or an external component of the housing, such as a header. The inductive elements serve to condition therapeutic stimulations such that varying the output of the generator allows the system to deliver arbitrary effective waveforms to the target tissue.

15 Claims, 10 Drawing Sheets

SYSTEM TO CREATE ARBITRARY WAVEFORMS USING AN EXTERNAL INDUCTOR AND AN IMPLANTABLE MEDICAL DEVICE

FIELD OF THE INVENTION

The invention relates to the field of implantable medical devices and more particularly to implantable stimulation devices, stimulation leads, and inductive filter elements external to the stimulation devices to deliver stimulation waveforms shaped for more efficient delivery of the therapeutic stimulation and for reduced pain sensation.

BACKGROUND OF THE INVENTION

Tachycardia refers generally to health ailments wherein one or more chambers of the patient's heart are contracting at an abnormally high rate. Fibrillation refers to a particularly dangerous tachycardia condition wherein one or more chambers are contracting in a rapid chaotic manner such that effective pumping from the affected chamber effectively ceases or is at least markedly reduced. Atrial fibrillation, while reducing overall heart efficiency by reducing the effective filling of the ventricles and presenting an elevated risk of thrombosis in certain patients, is generally not an immediately life-threatening condition. Ventricular fibrillation, however, is immediately life-threatening due to the effective cessation of pumping blood from the heart and, if not rapidly interrupted and replaced with at least limited pumping effectiveness, is fatal.

Accordingly, implantable cardioverter defibrillators (ICDs) have been developed to provide ongoing monitoring and therapy for treatment of potential fibrillation conditions. ICDs generally function by automatically monitoring the patient's cardiac activity for possible onset of a fibrillation condition and, upon detection of such a condition, automatically generate and deliver a therapeutic stimulation configured to interrupt the heart's fibrillation in an attempt to restore effective contractions. The stimulation delivered to defibrillate a person's heart is a relatively high energy electrical shock (up to the order of tens of joules) delivered between implanted electrodes, at least one of which is typically in direct contact with the patient's cardiac tissue. Defibrillation waveforms are typically either monophasic, having a single polarity, or biphasic, having both positive and negative polarities. The defibrillation shock is typically realized by accumulating a charge in a relatively large capacitor drawing electrical energy from a battery of the ICD. A common waveform delivered to the patient is a well-known decaying waveform following the exponential discharge decay of the capacitor and which is frequently gated or truncated after partial discharge of the charged capacitor. The waveforms are clipped or truncated in this manner to reduce the likelihood of retriggering an arrhythmia with a tailing discharge of the capacitor.

Several design and patient care considerations present themselves in the implementation of implantable cardioverter defibrillators. First, as previously noted, the energy typically required to defibrillate a patient is relatively large, e.g., on the order of tens of joules. As the implantable devices depend on a battery for their operating power, including generation and delivery of the defibrillation shocks, the energy draw to charge and deliver a defibrillation shock is a significant design consideration in implementing an ICD. The ICDs are desirably as small as possible to reduce discomfort and inconvenience to the implantee, however, reducing the size of the implantable device correspondingly reduces the volume available for the battery, as well as other components of the implantable device.

Secondly, the relatively high energy shock delivered to defibrillate the patient can be extremely painful and traumatic in many applications. The ICD automatically monitors the patient for indications of fibrillation and can frequently determine a fibrillation condition and prepare and deliver a therapeutic defibrillation shock pre-syncope, e.g., while the patient is still conscious. Such shocks delivered to a conscious patient can be extremely painful and anxiety and anticipation of aperiodic delivery of painful stimulation can contribute to development of psychological trauma in many patients.

Thus, it will be understood that there is a strong desire to effectively defibrillate a patient with a lower energy and/or voltage shock both to reduce the energy draw on the battery, thereby facilitating use of smaller batteries, as well as to extend the useful life between elective battery replacement explantation and implantation procedures. Reducing the voltage of the defibrillation shock also reduces the pain sensation and psychological trauma experienced by the recipient.

In response to these goals, a variety of alternative defibrillation shock waveform generators have been developed to provide alternatives to the truncated exponential decay of a simple capacitive discharge. For example, U.S. Publication 2001/0031991 to Russial teaches a circuit for producing a defibrillation waveform having an arrangement of a relatively complicated controlled voltage source added in the return path of the patient as connected to the charge capacitor to control the current delivered to the patient. U.S. Pat. No. 6,208,896 to Mulhauser teaches an apparatus for providing defibrillation waveforms including step-up and step-down converters, but which delivers a relatively jagged and inefficient defibrillation shock to the patient. As previously noted, arrangements to provide advantageous alternative defibrillation shocks must also take into consideration the strong design goals of maintaining a desirably compact implantable device to limit discomfort and inconvenience to the implantee, thereby limiting the use of relatively bulky components, such as inductors, within the devices.

Thus it will be appreciated that there is a desire for an ICD system which can deliver defibrillation shocks more efficiently and less painfully to a patient while not significantly expanding the physical envelope and weight of the device. It would be desirable to provide such improved ICD systems while avoiding significant additional circuit and control system complexity. It would be particularly desirable for a system to enhance the waveform efficiency and/or reduce the pain stimulus of existing alternative waveform generators, such as via a supplement or retrofit.

SUMMARY OF THE INVENTION

The aforementioned needs are satisfied by the invention which, in one embodiment, is an implantable stimulation system comprising an implantable housing, a stimulation current generator selectively generating therapeutic stimulations and encased within the housing, at least one implantable stimulation lead connected to the stimulation current generator and configured to deliver the therapeutic stimulations generated by the current generator to target patient tissue, and at least one inductive element arranged to condition the stimulation current for increased efficiency of delivery of the current to the target patient tissue and wherein the inductive element is arranged externally of the housing.

Another embodiment is an implantable stimulation system comprising an implantable housing, a stimulation current generator selectively generating therapeutic stimulations of multiple configurations and wherein the current generator is encased within the housing, at least one implantable stimulation lead connected to the stimulation current generator and configured to deliver the therapeutic stimulations generated by the current generator to target patient tissue, and at least one inductive element arranged to condition the therapeutic stimulations received from the stimulation current generator so as to deliver arbitrary conditioned effective waveforms to the target patient tissue having different morphologies than the configurations generated by the stimulation current generator and wherein the inductive element is arranged externally of the housing.

Yet another embodiment is a delivery circuit configured for connection to an implantable stimulation device, wherein the delivery circuit receives non-continuous stimulation energy from the implantable device and wherein the delivery circuit inductively accumulates portions of the stimulation energy during periods of delivery of the stimulation energy and returns accumulated energy to target tissue during periods of non-receipt of the stimulation energy such that effective stimulation energy as delivered to the target tissue is substantially continuous.

A further embodiment is an inductive element, wherein the inductive element is configured for implantation in a patient and for interconnection with an implantable stimulation device and an implantable stimulation lead and wherein, in an interconnected state, the inductive element is positioned external to the implantable stimulation device. Various embodiments thus provide inductive circuit elements arranged externally to the implantable stimulation pulse generator assembly which can filter or condition a relatively choppy modulated output and deliver a smoothed or conditioned effective waveform to the target patient tissue having a more continuous morphology. The inductive element(s) can be formed integrally with implantable stimulation leads either in a flexible lead body and/or in a substantially rigid header or bifurcation structure. The inductive element(s) can also be configured as separate components positionable between an implantable stimulation device housing and implantable lead. These and other objects and advantages of the invention will become more apparent from the following description taken in conjunction with the accompanying drawings.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
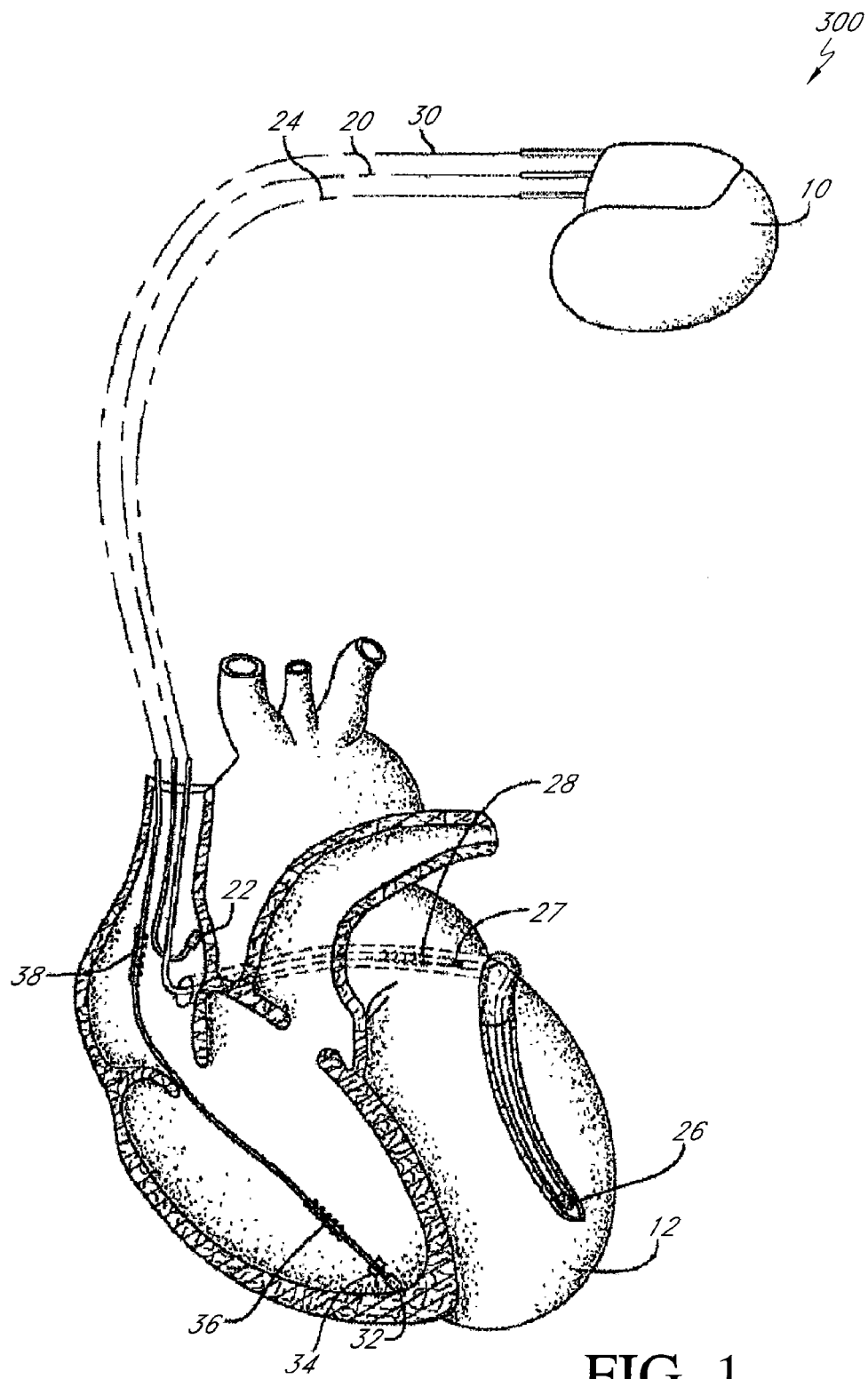
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
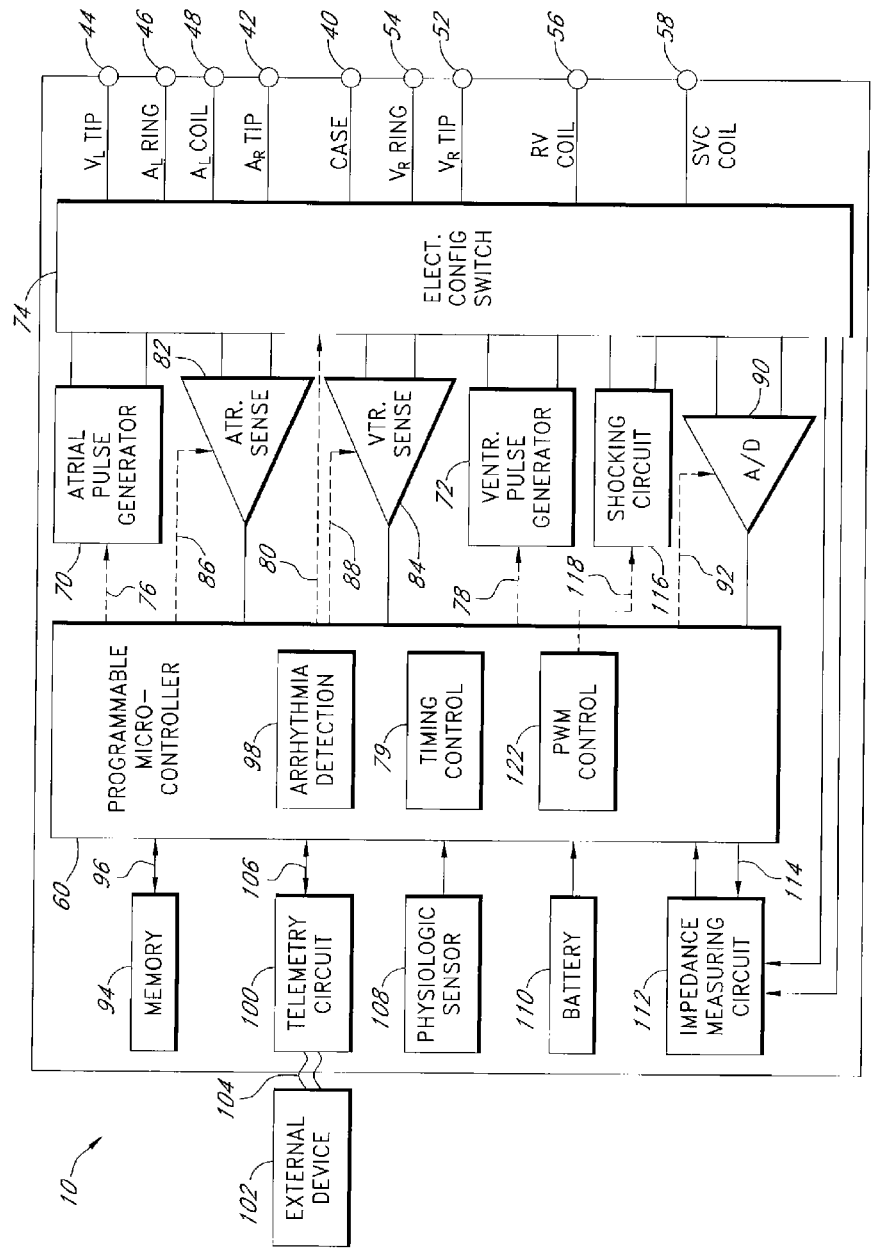
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection 98, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia.

The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, e.g., pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. In one embodiment, the control signal 118 is provided by a pulse width modulation (PWM) control 122 such that the shocking circuit 116 can provide a modulated pulsed shock output. The shocking circuit 116 generates shocking pulses of low (up to 0.5 joules), moderate (0.5-10 joules), or high energy (11 to 40 joules), as controlled by the microcontroller 60.

Such shocking pulses are applied to the patient's heart 12 through at least two shocking electrodes, and as shown in this embodiment, are selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
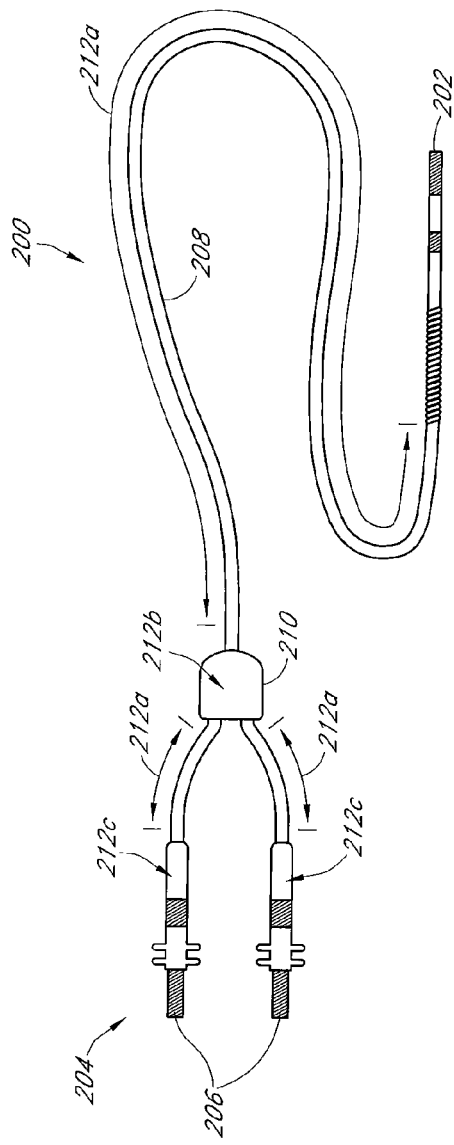
FIG. 3 illustrates embodiments of implantable stimulation leads and of placement of inductive elements incorporated with the lead.

FIG. 3 illustrates several embodiments of implantable stimulation leads 200 which are configured to more efficiently deliver cardioversion/defibrillation shocks to a patient and to do so with reduced pain sensation. The following description of embodiments of the implantable stimulation leads 200 and shocking systems 300 will focus on advantages provided by the various embodiments of the invention with respect to stimulation, however, it will be understood from the foregoing description that in certain embodiments, components and control systems are also utilized for sensing functions. The stimulation leads 200 generally define a distal end 202 with one or more electrodes configured for delivery of therapeutic stimulation and/or sensing of physiologic signals. The leads 200 also define a proximal end 204 configured for connection of the leads 200 to the implantable device 10. In this embodiment, this connection is provided by two connectors 206 which are joined to a lead body 208 via a bifurcation 210. The lead body 208 and bifurcation 210 comprise one or more conductors enclosed within biocompatible insulative material to conduct electrical signals between the electrodes at the distal end 202 and the connectors 206. The conductors are obscured from view by the insulative material of the lead body 208, bifurcation 210 and connectors 206 in FIG. 3. The connectors 206 are further configured for interconnection to the implantable device 10 such that the connectors 206 are interconnected to internal circuitry of the implantable device 10 as described above and further so as to seal the connection between the connectors 206 and the implantable device 210 against intrusion of bodily fluids into the implantable device 10 and similarly leakage of materials and fluids from the interior of the implantable device 10.

In various embodiments, the implantable leads 200 further comprise one or more inductive elements 212 indicated generally as 212a, 212b, and/or 212c depending upon their relative placement and construction. The inductive elements 212 are, in this embodiment, incorporated within the structure of the implantable lead 200 in such a manner as to be electrically in series between the electrodes and the connectors 206 and thus in series between the electrodes and the internal circuitry of the implantable device 10 to which the electrodes are connected via the internal conductors of the leads 200. Thus the inductive elements 212a, 212b, and/or 212c provide an inductive load outside of the implantable device 10 which is utilized to condition delivery of therapeutic stimulation for increased efficiency and reduced pain sensation as described in greater detail below following a description of the physical structure of the various embodiments of the inductive elements 212.

Figure 4:
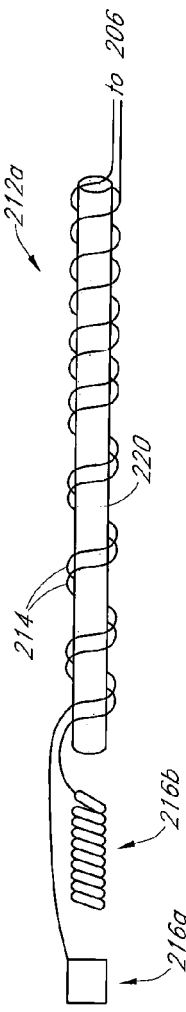
FIG. 4 illustrates one embodiment of a flexible ferromagnetic core inductive element suitable for incorporation in an implantable stimulation lead.

The inductive elements 212a, of which embodiments are illustrated in greater detail in FIG. 4, comprise a distributed inductive structure comprising coiled insulated conductors 214, which are wrapped in a helical manner about a centrally disposed flexible ferrite core 220. The flexible ferrite core 220 comprises ferromagnetic particles dispersed within and combined with a flexible silicon matrix to provide increased inductance for the inductive elements 212a. The flexible ferrite core 220 maintains the flexible nature of the lead body 208 to facilitate both the implantation of the leads 200 along a curved implantation path, as well as to accommodate movement of the patient and reduce stress and strain on the lead 200 throughout the implantation period.

In the particular embodiment illustrated in FIG. 4, insulative biocompatible material would typically define the outer surface of the lead body 208 leaving stimulation electrodes 216a, 216b exposed for contact with patient tissue, however covering and providing structural support for the remaining components of the stimulation lead 200 with lead body 208. This insulative material is omitted in FIG. 4 for clarity of illustration and understanding of the enclosed structures. In this particular embodiment, a pair of insulated conductors 214 is wrapped in a multi-filar configuration. Terminal distal ends of the insulated conductors 214 are electrically conducted in this particular embodiment to a pair of stimulation electrodes 216a, 216b, such as a ring or tip electrode and a relatively large area shocking coil or shock electrode. The insulated conductors 214 extend in the opposite direction through the lead body 208, through the bifurcation 210, and through the connectors 206 and would thus be connected on the proximal end 204 of the stimulation lead 200 to internal circuitry of the implantable device 10, such as for delivery of therapeutic stimulation.

Figure 5:
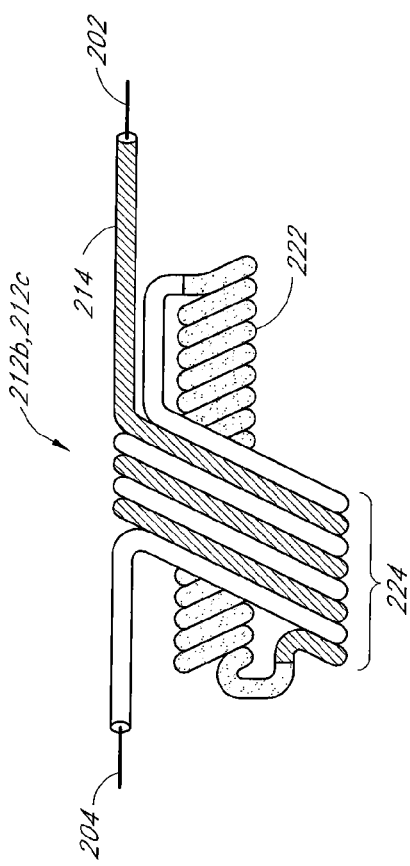
FIG. 5 illustrates one embodiment of a multiple winding air-core inductive element suitable for incorporation in an implantable stimulation lead.

FIG. 5 illustrates another embodiment of an inductive element 212 suitable for placement in the stimulation lead 200 generally in the region of the bifurcation 210 as inductive element 212b and/or generally in the location of one or more connectors 206, such as indicated by inductive elements 212c. In one particular embodiment, the inductive elements 212b, 212c comprise a concentric coil inductor structure lacking the ferromagnetic core, e.g., in the embodiments illustrated in FIG. 4. In one particular embodiment illustrated in FIG. 5, an insulated conductor 214 is wrapped to define an inner coil 222 of a single-filar configuration and which is over-wrapped with an outer coil 224 of a two-filar configuration. Opposite ends of the insulated conductor 214 would then terminate in a similar manner to that previously described for the embodiments illustrated in FIG. 4, for example, at a proximal end 204 with a connector 206 and at a distal end 202 at a stimulation electrode 216a, 216b. In this embodiment, the inner coil 222 and outer coil 224 are wrapped in opposite directions in two layers such that current passing along the insulated conductor 214 passes towards the distal end 202 coiled first in one direction and secondly in the opposite direction. This arrangement of the concentric inner 222 and outer 224 coils effectively increases the number of turns of the inductive element 212b, 212c. The inductance of the element 212 would thus increase as the square of the number of turns.

A further advantage of the embodiments illustrated in FIG. 5 is that the core of the inductive element 212b, 212c in these embodiments comprises air rather than a ferromagnetic core subject to magnetic saturation. In these embodiments, the inductive elements 212b, 212c have inductances on the order of tens of microhenries in the space envelope of a 7 French lead and with a length of the inductive elements 212b, 212c, on the order of two to four centimeters in length. In certain embodiments, an arrangement of inductive elements 212a of embodiments similar to those illustrated in FIG. 5 are provided as one or more relatively short inductive elements 212a with regions of the flexible lead body 208 interposed between the relatively rigid inductive elements 212a with adequate spacing to maintain the desired degree of overall lead flexibility and so as to inhibit stress concentration zones.

Figure 6:
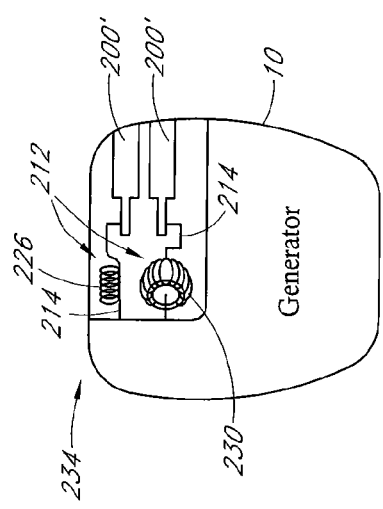
FIG. 6 illustrates embodiments of separate cylindrical and torroidal configuration inductive elements arranged in the header area between an implantable stimulation device and the implantable leads.

FIG. 6 illustrates yet other embodiments of inductive elements configured for placement generally in a header region 234 of the implantable device 10 and more particularly a generally cylindrical inductive element 226 and a generally torroidal inductive element 230. In these embodiments, both of the cylindrical inductive element 226 and the torroidal inductive element 230 are substantially rigid in structure. The generally cylindrical inductive element 226, as well as the general torroidal inductive element 230 further comprise ferromagnetic cores configured generally in a cylindrical or torroidal shape, respectively, about which corresponding insulated conductors 214 are wrapped in a known manner to provide the electrically inductive properties of the inductive elements 226, 230. The inductive elements 226, 230 would also be encased in a protective biocompatible material to both protect the inductive elements 226, 230 against the erosive effects of bodily fluids, as well as to protect the patient from possible deleterious effects from exposure to the materials comprising the inductive elements 226, 230, such as ferrite materials comprising the respective ferromagnetic cores. However, in FIG. 6, this biocompatible material is omitted for clarity of view of the underlying structures.

It will be further noted in the embodiments illustrated in FIG. 6 that the inductive elements 226, 230 are connected in serial arrangement with respective implantable stimulation leads 200'. The implantable stimulation leads 200' are substantially similar to the leads 200 previously described, however, the leads 200', as illustrated in FIG. 6 are interconnected to the inductive elements 226 and 230 which are configured as separate components.

One common feature among the implantable stimulation leads 200, 200' as illustrated in FIG. 3 through FIG. 6 is that the one or more inductive elements 212, 226, 230 are located outside of the implantable device 10. Thus, whether embodied as separate and/or continuous inductive elements 212a located generally in the lead body 208, inductive elements 212b located generally in a bifurcation 210 of a bifurcated lead 200, as inductive elements 212c located generally in one or more connectors 206, and/or as inductive elements 226, 230 interconnected as separate components between one or more implantable leads 200' and the implantable device 10, the inductive elements 212, 226, 230 do not occupy limited interior space of the implantable device 10.

Thus, in these embodiments of the invention, the inductive elements 212, 226, 230 can be provided as part of an implantable shocking system 300 without requiring an enlargement of the implantable device 10 nor a reduction in the available volume for other components of the device 10, such as batteries or high voltage storage capacitors, while maintaining a given volume for the device 10. Thus, the various embodiments of inductive elements 212, 226, 230 provide the ability to add inductive circuit elements to the implantable shocking system 300 in a manner that does not require an increase in the size of the implantable device or a reduction in its capacity. Various advantages of the inductive elements 212, 226, 230 with respect to the efficiency of delivery of therapeutic shocks, as well as the reduction in the pain sensation experienced by the patient upon delivery of shocks, will be described in greater detail with the following electrical circuit configurations of the implantable shocking system 300 as implanted within a patient and with the patient performing part of a terminus 302 (FIGS. 7-10) of the shocking system 300.

Figure 7:
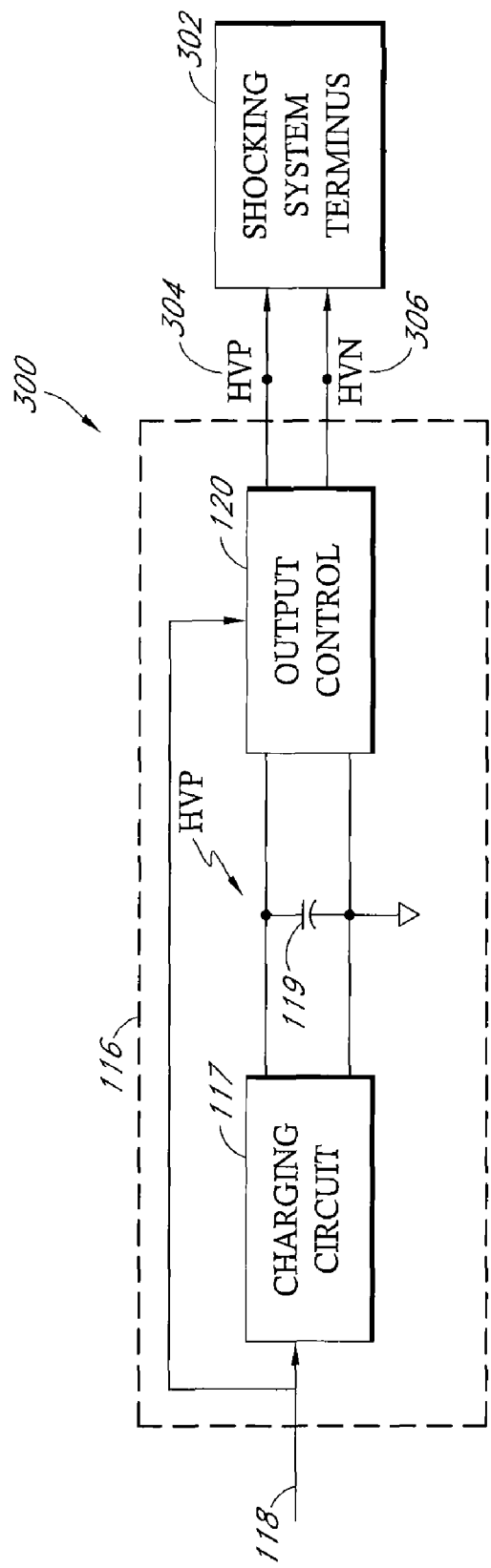
FIG. 7 is a high-level block diagram of one embodiment of an implantable circuit for generating arbitrary waveforms.

FIG. 7 is a high level block diagram illustrating one embodiment of the shocking circuit 116 as connected to a shocking system terminus 302 which together define an implantable shocking system 300. As previously described, in one embodiment the control signal 118 is generated by the PWM control 122 of the microcontroller 60 to regulate the generation and delivery of a therapeutic shock. The shocking circuit 116 generally includes a charging circuit 117 and an output control circuit 120. The output circuit 116 further includes one or more high voltage capacitor(s) 119 for temporary intermediate storage of shocking energy. The charging circuit 117 may be of a type well known in the art for charging the capacitor(s) 119 to a desired level. Once the capacitor is charged, under control of the PWM control 122 via the control signal 118, a relatively high-potential output voltage (HVP-HVN) will reside across the capacitor 119. This stored voltage is modulated by the output control 120 to produce a stimulation output having a desired waveform.

Figure 11:
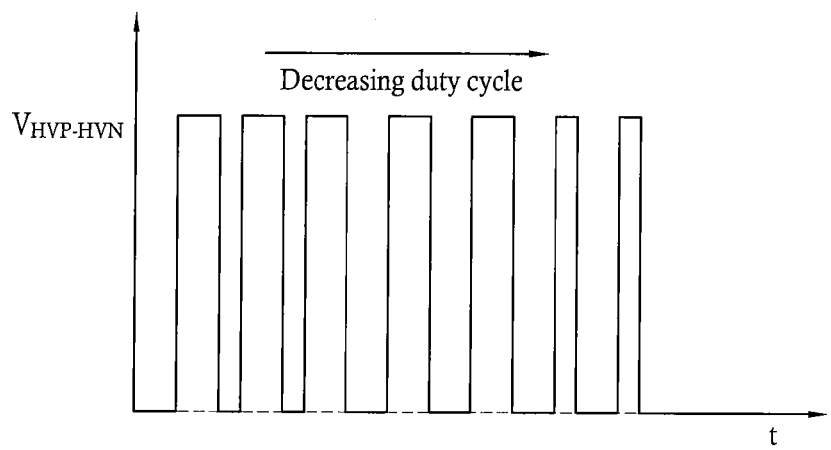
FIG. 11 illustrates a waveform corresponding to one embodiment of a modulated shocking stimulation.
Figure 14:
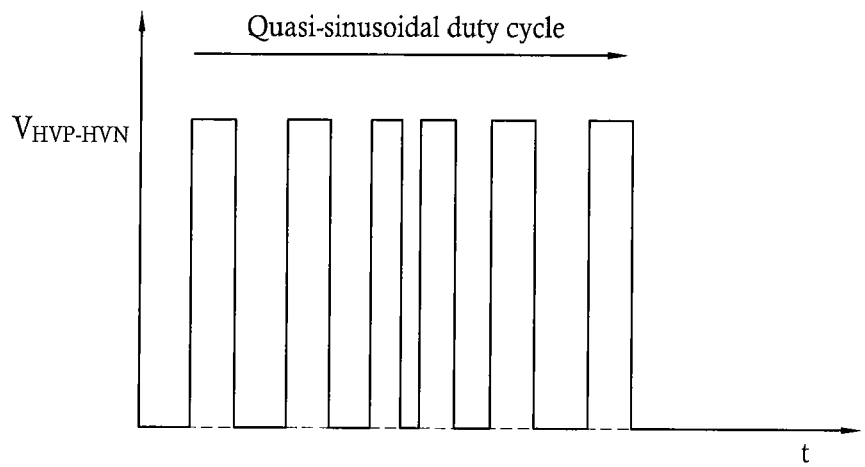
FIG. 14 illustrates a waveform corresponding to another embodiment of a modulated shocking stimulation.

In general, the output control 120 induces the shocking circuit 116 to deliver a modulated high voltage output, such as a pulse width modulated (PWM) output, to produce a rough stimulation output alternating between active periods or periods of energy delivery and non-active periods or periods wherein the stimulation output is temporarily isolated from the terminus 302 (FIGS. 11 and 14). Additional details of embodiments of shocking circuits suitable for use with the embodiments of the invention described herein can be found in the co-owned U.S. application entitled "Implantable Cardiac Stimulation Device Including an Output Circuit that Provides Arbitrarily Shaped Defibrillation Waveforms", Ser. No. 10/687,386, filed Oct. 15, 2003 which is incorporated herein in its entirety.

Thus, the output of the shocking circuit 116 is provided between nodes 304 and 306 which are indicated as high voltage positive (HVP) and high voltage negative (HVN), respectively. As previously described, the output of the shocking circuit 116 is provided as a modulated output such as the previously described embodiments of a pulse width modulated output. It will be appreciated that various parameters of the modulated output can be varied to achieve the desired shock for delivery to the patient. These parameters include the amplitude of the pulses, the "width" or duration of the pulses, and/or the duty cycle or proportion of time at which the output is active. The load to which the output of the shocking circuit 116 is provided is indicated generally as the shocking system terminus 302 and in the following descriptions, this terminus 302 includes the implantable stimulation leads 200, 200' with one or more inductive elements 212, 226, and/or 230 incorporated either with the leads 200 or formed as separate components in combination with the leads 200'. The shocking system terminus 302 also includes the electrical load of the patient and it is this portion of the terminus 302, e.g., the target tissue of the patient, which receives particular benefit from the various embodiments described herein.

Figure 8:
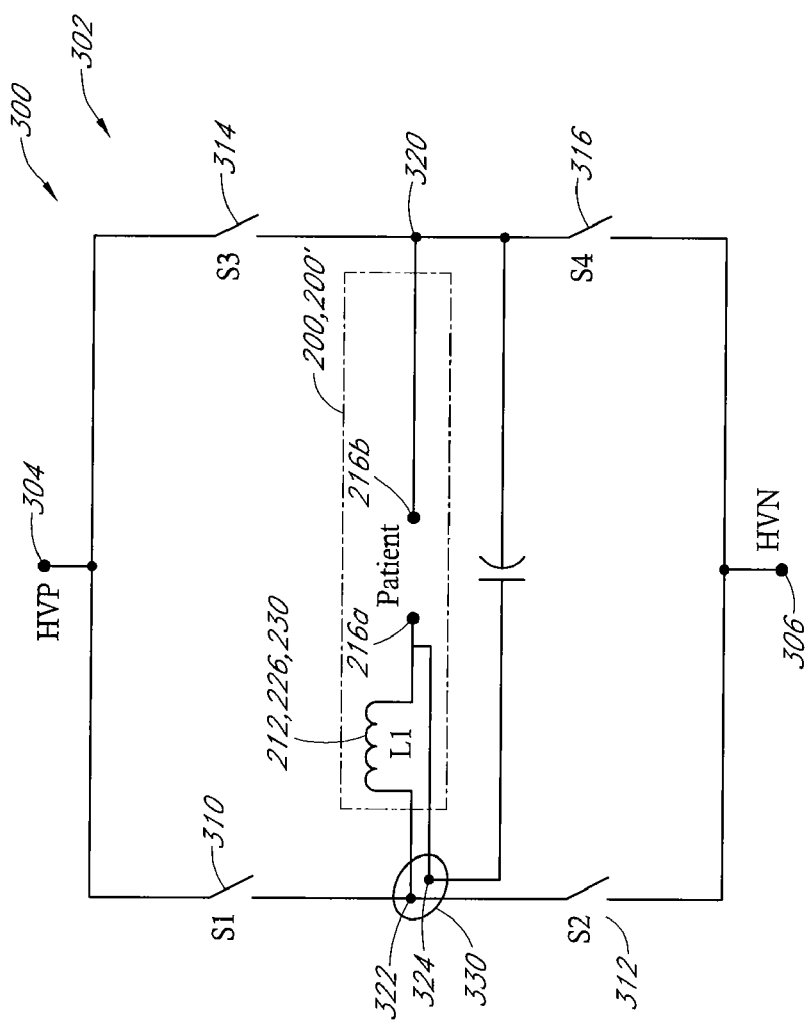
FIG. 8 is a circuit diagram of one embodiment of a terminus circuit, including a patient load, for delivery of therapeutic shocks.

FIG. 8 illustrates a circuit schematic diagram of one embodiment of a shocking system terminus 302, which is provided with an output from the shocking circuit 116 between the nodes 304 and 306 also identified as HVP and HVN, respectively. Also, as previously noted, delivery of therapeutic shocks from the shocking circuit 116 can occur in either a monophasic or biphasic manner depending upon the particular indications and therapeutic requirements of the individual patient. The following description will be made with respect to a monophasic delivery of therapy for brevity of description, however, it will be well understood by one of ordinary skill in the art that a complimentary reversal of applied and resultant voltages and currents can be provided to effect a biphasic stimulation.

The electrical circuit of the shocking system terminus 302 also defines in this embodiment a node 320 corresponding in one embodiment to the case or housing 40 of the implantable device 10 acting as a stimulation electrode and also identified in FIG. 8 as electrode or node 216b. The electrical circuit of the shocking system terminus 302 also defines a node 322, which can correspond in this embodiment to a proximal connection between a connector 206 of a lead 200 and the implantable device 10. The electrical circuit of the shocking system terminus 302 also defines a node 324, which is common with another electrode 216a such as a shocking electrode of the lead 200.

The shocking system 300 also includes a plurality of switches arranged and configured to desirably conduct and isolate applied voltages, such as from the shocking circuit 116, to control delivery of shock therapy provided to the patient. In one particular embodiment, a switch S1 310 is connected between the node 304 and node 322, a switch S2 312 is connected between the node 322 and node 306, a switch S3 314 is connected between the node 304 and node 320, and a switch S4 is provided between the node 320 and node 306. A capacitor 326 is connected between the node 324 and the node 320 in this embodiment, e.g., in parallel with the patient. One or more inductive elements 212, 226, and/or 230 are connected between the node 322 and node 324 and as previously noted. The one or more inductive elements 212, 226, 230 can be incorporated either within the lead 200 or as a separate component interconnected between the lead 200' and the implantable device 10. The one or more inductive elements 212, 226, and/or 230 are indicated generally as L1 and the total inductance of multiple inductive elements interconnected together can be readily determined according to well understood principles by one of ordinary skill in the art. Thus, the electrical circuit of the shocking system terminus 302 as interconnected to the patient, wherein the patient defines an element of the circuit, can be considered to define an H-bridge, including the switches S1, S2, S3, and S4, 310, 312, 314, 316, respectively, the one or more inductive elements 212, 226, 230, the patient, and the capacitor 326. Thus, the switches S1 through S4 can be opened or closed to provide multiple applied voltages across the center leg of the H bridge, e.g., between nodes 322 and 320.

Figure 9:
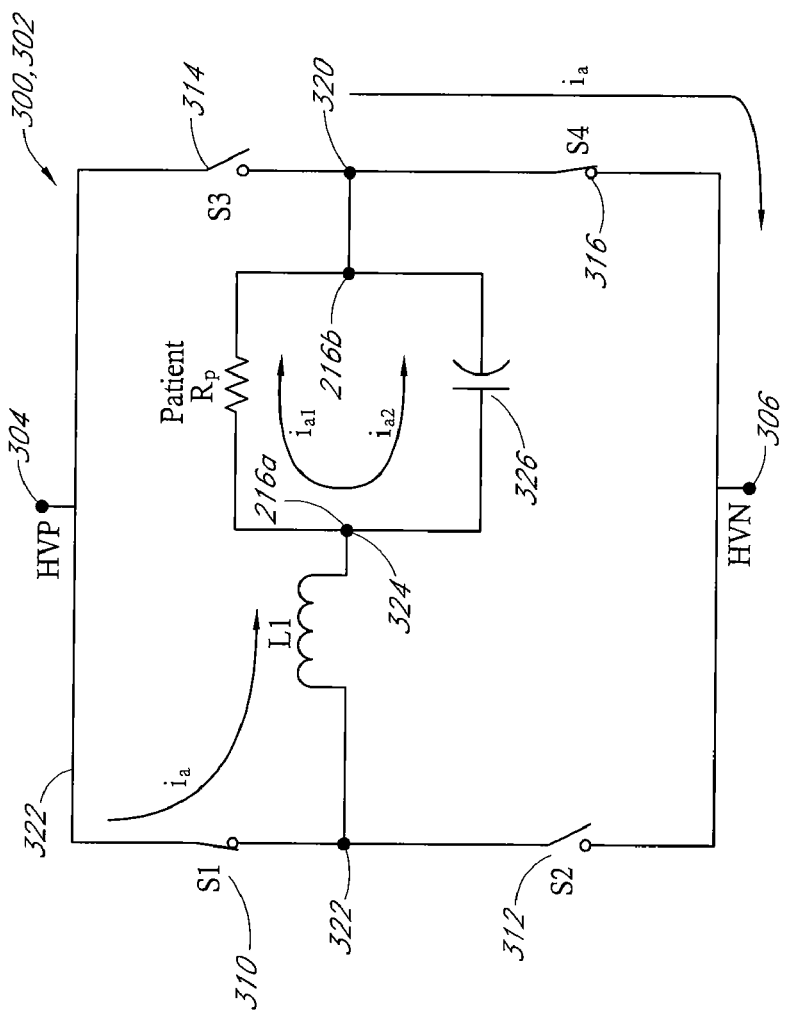
FIG. 9 is a circuit diagram of the circuit of FIG. 8 during an accumulation phase of operation.

FIG. 9 illustrates one embodiment of an accumulation configuration 332 wherein switches S1, 310 and S4, 316 are closed and switches S2, 312 and S3, 314 are opened. The timing of the respective opening and closing of the switches S1 through S4 is preferably coordinated with the modulated delivery from the shocking circuit 116 to the nodes 304, HVP and nodes 306, HVN to substantially coincide with the active periods of the modulated output from the shocking circuit 116. Again, description will be made with respect to a monophasic shock delivery, however, complimentary reversal of polarities and switch open/closed status can be readily affected to provide a biphasic stimulation shock.

Thus, with potential applied between nodes 304 and 306, an accumulation current $i_a$ through switch S1 310 and the one or more inductive elements indicated in general as L1 and similarly through switch S4 316 between the node 320 and node 306. A portion of the accumulation current $i_a$ will flow through the patient with this current being indicated as $i_{a1}$ and with the remaining portion indicated as $i_{a2}$ flowing through the capacitor 326. Thus, the load of the patient indicated as $R_p$ forms a branch of the electrical circuit of the shocking system terminus 302. While the patient load is indicated schematically as a resistive element $R_p$, it will be appreciated that the patient tissue will also exhibit some inductive and capacitive load characteristics.

Figure 10:
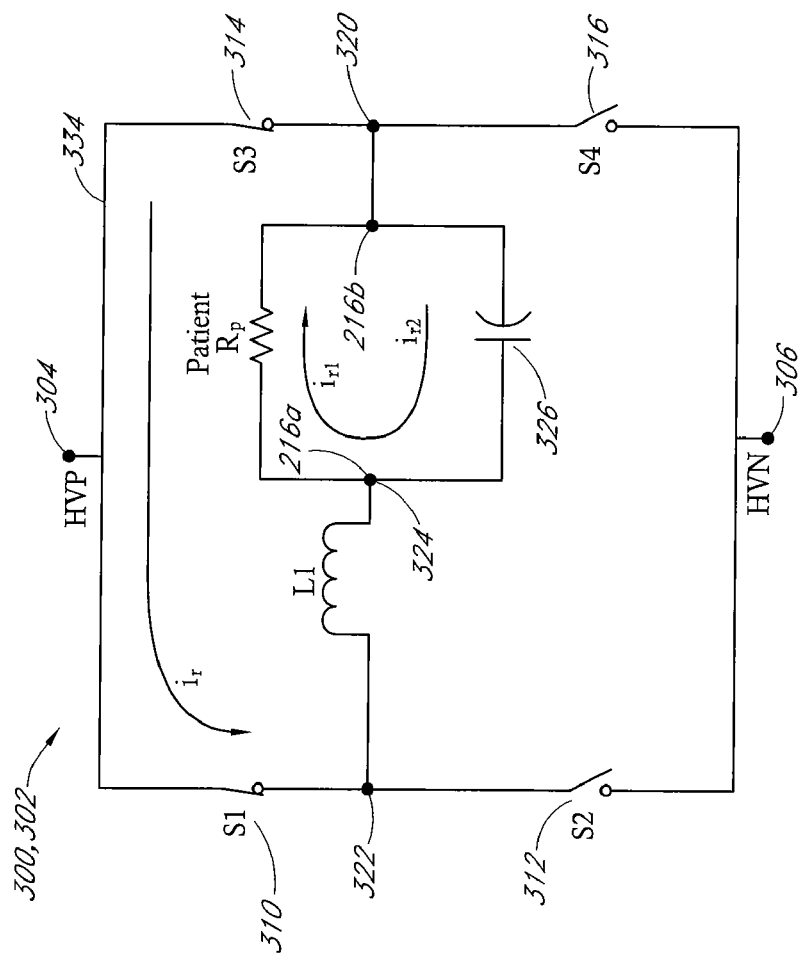
FIG. 10 is a circuit diagram of the circuit of FIG. 8 during a discharge phase of operation.

FIG. 10 illustrates a subsequent relaxation configuration 334 which alternates with the accumulation configuration 332 to increase efficiency of the delivery of the therapeutic shock to the patient. The relaxation configuration is defined by the closing of switch S1, 310 and switch S3, 314 with the opening of switches S2, 312 and S4, 316. As both switches S2, 312 and S4, 316 are opened any voltage provided between nodes 304 and 306 is removed from the shocking system terminus 302, however, the switching to the relaxation configuration is preferably coordinated with the modulation of the output from the shocking circuit 116 to substantially coincide with the non-active periods of the modulated output of the shocking circuit 116.

In the relaxation configuration 334, a relaxation current $i_r$ will flow through switches S3 314 and S2 310 and through the inductive element L1. This will sum at node 324 with a relaxation current through the capacitor 326 indicated in FIG. 10 as $i_{r2}$ and the relaxation current through the patient load $R_p$ indicated in FIG. 10 as $i_{r1}$. Thus, the shocking system terminus 302 with the patient load can be considered to define a second order filter circuit, including the inductive portion L1, the capacitor 326, and the largely resistive patient load indicated as $R_p$. In one particular embodiment, with component values of the total inductance of the inductive elements 212, 226, and/or 230 of approximately 10 microhenries, a capacitance of the capacitor 326 of approximately one microfarad and a resistive patient load $R_p$ of approximately 5 ohms gives a damping coefficient α of approximately 10,000 and an undamped or natural frequency ω of approximately 300,000 with ω>α or an under-damped condition.

FIG. 11 illustrates one embodiment of the output of the shocking circuit 116 feeding into the shocking system terminus 302. In this particular embodiment, FIG. 11 illustrates that the output of the shocking circuit 116 exhibits a substantially constant output amplitude and a progressively decreasing duty cycle throughout delivery of the therapeutic shock. The amplitude of the output of the shocking circuit 116 in this embodiment is in the range of approximately 300 to 400 volts.

Figure 12:
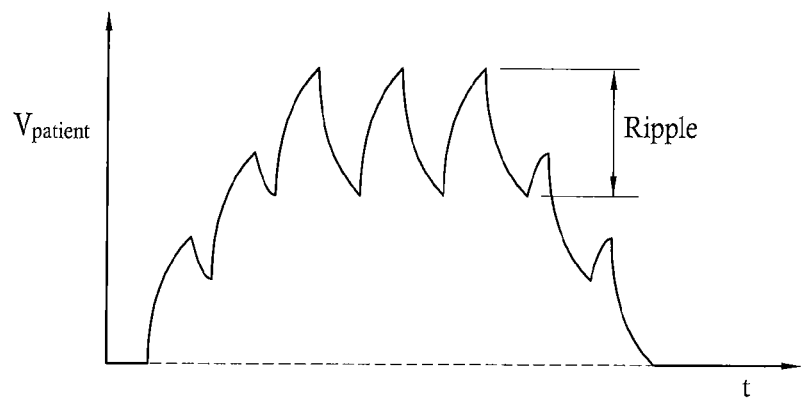
FIG. 12 illustrates one embodiment of a partially conditioned stimulation waveform intermediate the shocking circuit and the target tissue.

FIG. 12 is a schematic illustration of an output waveform as seen across the stimulation electrodes, in this embodiment electrodes 216a, 216b, or across the patient and more particularly illustrating the influence of the inductive elements 212, 226, 230 in conditioning the output from the shocking circuit 116 to a smoother more efficient waveform. In particular, FIG. 12 illustrates the exponential rise and decay of the therapeutic shock as seen across the patient electrodes throughout the alternating accumulation and relaxation configurations 232, 234, respectively, of the shocking system terminus 302.

Figure 13:
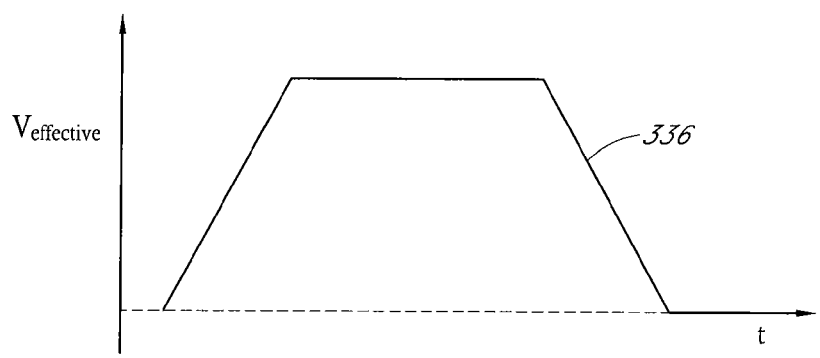
FIG. 13 illustrates one embodiment of a conditioned effective stimulation waveform as delivered to the target tissue.

FIG. 13 illustrates schematically a further waveform indicated as $V_{effective}$ representative of the stimulation shock waveform effectively seen at cell membranes of the target tissue in the patient's heart. As can be seen by a comparison of the relatively abrupt transitions between the full voltage and zero output of the modulated shocking circuit 116 output of FIG. 11 to the relatively smooth ramp-up, hold, and ramp-down effective waveform experienced at the target cells in the patient's heart, that the shocking system terminus 302 significantly conditions the input waveform. This conditioned waveform 336 exhibits a generally trapezoidal morphology and has been seen to more efficiently defibrillate a patient, e.g., to effectively defibrillate the patient with reduced power consumption from the battery 110 of the implantable device 10 and with a reduced pain sensation experienced by the patient. In certain applications, up to a fourfold decrease in pain/four times increase in patient pain threshold has been observed.

Figure 15:
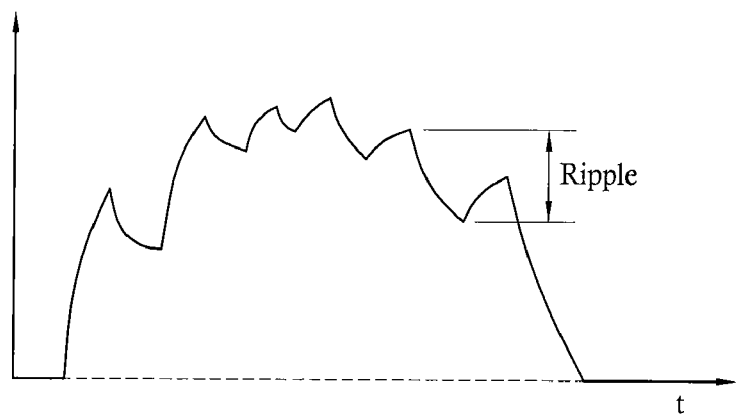
FIG. 15 illustrates another embodiment of a partially conditioned stimulation waveform intermediate the shocking circuit and the target tissue.
Figure 16:
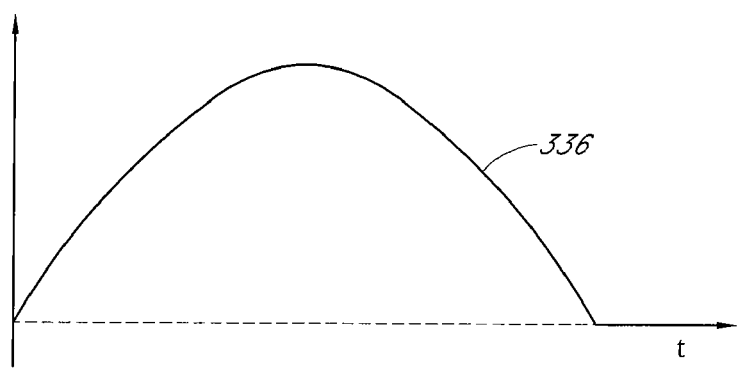
FIG. 16 illustrates another embodiment of an effective conditioned stimulation waveform as delivered to the target tissue.

FIGS. 14-16 illustrate another embodiment of a modulated output from the shocking circuit 116 having a different, quasi-sinusoidal duty cycle (FIG. 14), the corresponding partially conditioned therapeutic stimulation as seen across the patient electrodes (FIG. 15), and the effective conditioned stimulation waveform as seen at the target patient tissue (FIG. 16). The conditioned effective waveform of the embodiment illustrated by FIG. 16 comprises a substantially half sine-wave morphology. This effective morphology is also more efficient at defibrillating the target tissue than other non-exponential decay waveforms and yet other arbitrary stimulation waveforms can be implemented in other embodiments based upon the illustration and description herein without detracting from the scope of the invention. It should also be understood that the illustrations of FIGS. 11-16 are schematic in nature illustrating the general principles of embodiments of the invention and that the illustrated waveforms should not be considered to be strictly to scale and proportional. For example, the ripple magnitude in FIGS. 12 and 15 and the substantial lack of any ripple in FIGS. 13 and 16 is exaggerated for illustrative purposes Thus, according to various embodiments of the invention, the inductive elements 212, 226, and/or 230 also illustrated in FIG. 9 and FIG. 10 by the combined designator L1, as well as the capacitor 326 provide storage elements for current and electrical potential respectively which enable a smoothing of the relatively abrupt transitions from the modulated output of the shocking circuit 116 to a more normalized or conditioned waveform 336 such as seen as in FIG. 13. Thus, the shocking system 300, by alternating periods of partial accumulation of electrical energy during delivery periods of a modulated source such as the output of the shocking circuit 116 and delayed delivery during non-delivery periods smoothes and tapers an effective stimulation waveform delivered to the target patient tissue such that the relatively abrupt stepped waveform output by the shocking circuit 116 is filtered for delivery to the target tissue. Similarly, this partially accumulated electrical energy is returned via the relaxation configuration 334 during non-active periods of a modulated output such as from the shocking circuit 116 such that the net stimulation waveform over time is normalized or conditioned to obtain a more efficient and thus less painful conditioned waveform 336, which can effectively defibrillate the patient with reduced overall power consumption.

The shocking system 300, in certain embodiments, provides this improved efficiency and reduced pain sensation via conventional passive circuit elements, including inductive elements 212, 226, and/or 230, with reduced need for relatively complex secondary controlled voltage sources or other active controlled components such as step-down, step-down converters, gates, etc. In various embodiments, the inductive elements 212, 226, 230 are provided to the shocking system 300 external to the implantable device 10 and thus provide improved system 300 performance without consuming valuable internal space inside the implantable device 10, thus, maintaining volume allocated to power sources such as the battery 110 and high voltage capacitor 119.

In certain embodiments, inductive elements 212a are distributed throughout the lead body 208 in a manner so as to maintain the flexibility of the lead body 208 to facilitate implantation and movement of the patient. In other embodiments, the inductive elements 212b, 212c, 226, and/or 230 are located outside of the flexible lead body either incorporated with an implantable lead 200 or as separate components interconnected with an implantable lead 200' and thus in these embodiments the inductive elements can exhibit a rigid structural characteristic without detracting from the flexibility of the lead body 208. Depending on the indications for a particular application, the inductive elements 212, 226, and/or 230 can be provided either as air core configuration to avoid magnetic saturation and/or can be provided with a ferromagnetic core to increase inductance per unit volume to facilitate reduction in size of the inductive elements 212, 226, and/or 230.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable stimulation system comprising:
   an implantable housing;
   a stimulation current generator selectively generating therapeutic stimulations and encased within the housing;
   at least one implantable stimulation lead connected to the stimulation current generator and configured to deliver the therapeutic stimulations generated by the current generator to target patient tissue; and
   at least one inductive element arranged to condition the stimulation current for increased efficiency of delivery of the current to the target patient tissue and wherein the inductive element is arranged externally of the housing
   wherein the stimulation current generator generates the therapeutic stimulations in a pulse modulated configuration having a first ripple magnitude between active and non-active pulses and wherein the at least one inductive element accumulates and returns electrical energy for delivery to the target patient tissue in an alternating manner so as to provide an effective stimulation to the target patient tissue having a lower second ripple magnitude.

2. The system of claim 1, further comprising a capacitive element arranged so as to condition the current before delivery to the target patient tissue.

3. The system of claim 2, wherein the capacitive element, the at least one inductive element, and the target patient tissue together define a second order filter circuit configured to condition the current.

4. The system of claim 1, wherein the stimulation current generator generates defibrillation therapeutic stimulations and wherein the conditioning increases the efficiency of the therapeutic defibrillation stimulations by reducing a total energy of the stimulations required from the stimulation current generator to effectively defibrillate the patient tissue.

5. The system of claim 1, wherein one or more of the inductive elements are incorporated within the implantable stimulation lead.

6. The system of claim 1, wherein one or more of the inductive elements is configured as a separate component interconnected between the stimulation current generator and a respective implantable stimulation lead.

7. An implantable stimulation system comprising:
   an implantable housing;
   a stimulation current generator selectively generating therapeutic stimulations of multiple configurations and wherein the current generator is encased within the housing;
   at least one implantable stimulation lead connected to the stimulation current generator and configured to deliver the therapeutic stimulations generated by the current generator to target patient tissue; and
   at least one inductive element arranged to condition the therapeutic stimulations received from the stimulation current generator so as to deliver arbitrary conditioned effective waveforms to the target patient tissue having different morphologies than the configurations generated by the stimulation current generator and wherein the inductive element is arranged externally of the housing;
   wherein the stimulation current generator generates a modulated output and wherein the system changes a duty cycle of the modulated output to deliver a desired arbitrary effective waveform.

8. The system of claim 7, wherein the modulated output is defined by alternating periods of active output and substantially absent output and wherein a corresponding arbitrary effective waveform is substantially continuous.

9. An implantable lead for delivery of therapy from an implantable stimulation device wherein the lead includes one or more structures arranged to inductively filter therapeutic currents provided by the implantable stimulation device before delivery to a patient.

10. The implantable lead of claim 9, wherein one or more of the inductive structures comprise a ferromagnetic core having ferromagnetic particles dispersed within a flexible matrix such that the ferromagnetic core and associated one or more inductive structures is flexible.

11. The implantable lead of claim 9, wherein one or more of the inductive structures are configured as a cylindrical inductor.

12. The implantable lead of claim 9, wherein one or more of the inductive structures are configured as a torroidal inductor.

13. The implantable lead of claim 9, wherein one or more of the inductive elements comprise multiple winding layers coiled in opposing directions.

14. The implantable lead of claim 9, wherein the lead comprises a flexible lead body and wherein one or more of the inductive structures is incorporated within the lead body so as to maintain the flexibility of the lead body.

15. The implantable lead of claim 9, wherein the lead defines a proximal end and wherein one or more of the inductive structures are substantially rigid and arranged adjacent the proximal end of the lead.

* * * * *